(12) United States Patent
Baril et al.

(10) Patent No.: US 11,751,875 B2
(45) Date of Patent: Sep. 12, 2023

(54) SURGICAL BUTTRESS ATTACHMENT ASSEMBLIES FOR SURGICAL STAPLING APPARATUS

(71) Applicant: Covidien LP, Mansfield, MA (US)

(72) Inventors: Jacob C. Baril, Norwalk, CT (US); Wojciech Kisiel, North Haven, CT (US)

(73) Assignee: COVIDEN LP, Mansfield, MA (US)

( * ) Notice: Subject to any disclaimer, the term of this patent is extended or adjusted under 35 U.S.C. 154(b) by 141 days.

(21) Appl. No.: 17/500,193

(22) Filed: Oct. 13, 2021

(65) Prior Publication Data

US 2023/0111108 A1 Apr. 13, 2023

(51) Int. Cl.
*A61B 17/072* (2006.01)

(52) U.S. Cl.
CPC .......... *A61B 17/07292* (2013.01); *A61B 2017/07264* (2013.01); *A61B 2017/07271* (2013.01)

(58) Field of Classification Search
CPC ............ A61B 17/07292; A61B 17/068; A61B 17/105; A61B 17/1155; A61B 17/1114
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 3,364,200 A | 1/1968 | Ashton et al. | |
| 3,499,591 A | 3/1970 | Green | |
| 3,797,494 A | 3/1974 | Zaffaroni | |
| 3,939,068 A | 2/1976 | Wendt et al. | |
| 3,948,666 A | 4/1976 | Kitanishi et al. | |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

European Office Action corresponding to EP 14 17 2681.0 dated May 13, 2016.

(Continued)

*Primary Examiner* — Nathaniel C Chukwurah
(74) *Attorney, Agent, or Firm* — CARTER, DELUCA & FARRELL, LLP

(57) ABSTRACT

A surgical buttress attachment assembly includes a staple cartridge having a cartridge body and a cartridge tip, and a surgical buttress. The cartridge tip includes a distal buttress attachment assembly including a block body disposed within a cavity defined in the cartridge tip and a distal tongue extending distally from the block body. The block body is movable between an extended position and a retracted position. A proximal end portion of the surgical buttress is releasably secured to the cartridge body and a distal end portion of the surgical buttress is releasably secured to the cartridge tip by engagement of the distal tongue with the distal end portion when the block body is in the extended position.

20 Claims, 11 Drawing Sheets

(56) References Cited

U.S. PATENT DOCUMENTS

| | | | |
|---|---|---|---|
| 4,416,698 A | 11/1983 | McCorsley, III | |
| 4,429,695 A | 2/1984 | Green | |
| 4,452,245 A | 6/1984 | Usher | |
| 4,473,077 A | 9/1984 | Noiles et al. | |
| 4,605,730 A | 8/1986 | Shalaby et al. | |
| 4,626,253 A | 12/1986 | Broadnax, Jr. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,057,334 A | 10/1991 | Vail | |
| 5,065,929 A | 11/1991 | Schulze et al. | |
| 5,112,496 A | 5/1992 | Dhawan et al. | |
| 5,162,430 A | 11/1992 | Rhee et al. | |
| 5,205,459 A | 4/1993 | Brinkerhoff et al. | |
| 5,263,629 A | 11/1993 | Trumbull et al. | |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A | 11/1998 | Yoon | |
| 5,843,096 A | 12/1998 | Igaki et al. | |
| 5,871,135 A | 2/1999 | Williamson, IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,957,363 A | 9/1999 | Heck | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,330,965 B1 | 12/2001 | Milliman et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 | 1/2003 | Grant et al. | |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,568,398 B2 | 5/2003 | Cohen | |
| 6,590,095 B1 | 7/2003 | Schleicher et al. | |
| 6,592,597 B2 | 7/2003 | Grant et al. | |
| 6,605,294 B2 | 8/2003 | Sawhney | |
| 6,610,006 B1 | 8/2003 | Amid et al. | |
| 6,627,749 B1 | 9/2003 | Kumar | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,656,200 B2 | 12/2003 | Li et al. | |
| 6,669,735 B1 | 12/2003 | Pelissier | |
| 6,673,093 B1 | 1/2004 | Sawhney | |
| 6,677,258 B2 | 1/2004 | Carroll et al. | |
| 6,685,714 B2 | 2/2004 | Rousseau | |
| 6,702,828 B2 | 3/2004 | Whayne | |
| 6,703,047 B2 | 3/2004 | Sawhney et al. | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,746,869 B2 | 6/2004 | Pui et al. | |
| 6,764,720 B2 | 7/2004 | Pui et al. | |
| 6,773,458 B1 | 8/2004 | Brauker et al. | |
| 6,818,018 B1 | 11/2004 | Sawhney | |
| 6,843,252 B2 | 1/2005 | Harrison et al. | |
| 6,896,684 B2 | 5/2005 | Monassevitch et al. | |
| 6,927,315 B1 | 8/2005 | Heinecke et al. | |
| 6,939,358 B2 | 9/2005 | Palacios et al. | |
| 6,946,196 B2 | 9/2005 | Foss | |
| 6,953,139 B2 | 10/2005 | Milliman et al. | |
| 6,959,851 B2 | 11/2005 | Heinrich | |
| 7,009,034 B2 | 3/2006 | Pathak et al. | |
| 7,025,772 B2 | 4/2006 | Gellman et al. | |
| 7,060,087 B2 | 6/2006 | DiMatteo et al. | |
| 7,087,065 B2 | 8/2006 | Ulmsten et al. | |
| 7,108,701 B2 | 9/2006 | Evens et al. | |
| 7,128,253 B2 | 10/2006 | Mastri et al. | |

(56) References Cited

U.S. PATENT DOCUMENTS

| | | | |
|---|---|---|---|
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 * | 5/2011 | Aranyi ............ A61B 17/07207 |
| | | 227/176.1 |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 * | 11/2012 | Aranyi ............ A61B 17/07292 |
| | | 227/176.1 |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |

(56) References Cited

U.S. PATENT DOCUMENTS

| | | |
|---|---|---|
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,828,023 B2 | 9/2014 | Neff et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 10,426,468 B2 | 10/2019 | Contini et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |

(56) References Cited

U.S. PATENT DOCUMENTS

| | | |
|---|---|---|
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |
| 2021/0290230 A1 | 9/2021 | Fernandes et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| EP | 3135215 A1 | 3/2017 |
| EP | 3441011 A1 | 2/2019 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.

(56) References Cited

OTHER PUBLICATIONS

Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
U.S. Appl. No. 17/329,711, filed May 25, 2021, entitled "Powered Stapling Device With Manual Retraction".
International Search Report and Written Opinion issued in corresponding International Application No. PCT/IB2022/059464 dated Dec. 21, 2022, 12 pages.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.

(56) References Cited

OTHER PUBLICATIONS

Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).

(56) References Cited

OTHER PUBLICATIONS

Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).

* cited by examiner

SURGICAL BUTTRESS ATTACHMENT ASSEMBLIES FOR SURGICAL STAPLING APPARATUS

FIELD

This disclosure generally relates to surgical stapling apparatus, and more particularly, to surgical buttress attachment assemblies for releasably securing surgical buttresses to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon. The buttress material reinforces the staple or suture line as well as covers the juncture of the body tissues to reduce leakage prior to healing.

SUMMARY

This disclosure relates to cartridge-side surgical buttress attachment onto a loading unit of a surgical stapling apparatus. Surgical buttress attachment assemblies of the disclosure are designed to make surgical buttress attachment a simple, straightforward, and cost-effective procedure. The surgical buttress attachment assemblies secure a surgical buttress to a staple cartridge of a surgical stapling apparatus and keep the surgical buttress taut until the surgical stapling apparatus is fired and the surgical buttress is released. Further, the surgical buttress attachment assemblies minimize or prevent the surgical buttress from being elongated and/or deformed during assembly, enabling the staple lines to remain flush with the surgical buttress so that staple formation is not adversely affected during use.

In aspects, this disclosure provides a surgical buttress attachment assembly for use with a surgical stapling apparatus that includes a staple cartridge and a surgical buttress. The staple cartridge includes a cartridge body and a cartridge tip extending distally from the cartridge body. The cartridge body has a tissue facing surface including staple pockets defined therein and the cartridge tip includes an inner surface extending distally from the tissue facing surface and defining an opening therethrough that is in communication with a cavity defined in the cartridge tip. The cartridge tip includes a distal buttress attachment assembly having a block body disposed within the cavity and a distal tongue extending distally from the block body. The block body is movable between an extended position in which a distal end of the distal tongue is disposed over the inner surface of the cartridge tip and a retracted position in which the distal end of the distal tongue is aligned with the inner surface. The surgical buttress includes a proximal end portion releasably secured to the cartridge body and a distal end portion releasably secured to the cartridge tip by engagement of the distal tongue with the distal end portion when the block body is in the extended position.

The tissue facing surface of the cartridge body may include a central longitudinal slot defined therein, and the distal tongue may be axially aligned with the central longitudinal slot.

The distal buttress attachment assembly may further include a resilient biasing member biasing the block body in the extended position. In some aspects, the resilient biasing member is a spring. In certain aspects, the spring includes a proximal end portion coupled to a distal-facing wall of the cartridge tip that defines the cavity and a distal end portion coupled to the block body, and the spring is compressible during axial movement of the block body between the extended and retracted positions. In some aspects, the resilient biasing member is a proximal arm extending from the block body. In certain aspects, the proximal arm abuts a distal-facing wall of the cartridge tip that defines the cavity, and the proximal arm is temporarily deformable against the distal-facing wall during rotational movement of the block body between the extended and retracted positions.

The staple cartridge may further include a proximal buttress attachment assembly including proximal posts extending outwardly from the tissue facing surface. The proximal end portion of the surgical buttress may be releasably secured to the cartridge body by engagement of the proximal posts with the proximal end portion. In some aspects, the proximal posts are proximal to the staple pockets. In some aspects, the tissue facing surface of the cartridge body includes a central longitudinal slot defined therein, and the proximal posts are disposed on opposed sides of the central longitudinal slot. The proximal end portion of the surgical buttress may define proximal openings therethrough configured to receive the proximal posts therethrough, and the distal end portion of the surgical buttress may define a distal opening therethrough configured to receive the distal tongue therethrough.

In aspects, this disclosure provides a surgical stapling apparatus including a handle assembly, an elongate body extending distally from the handle assembly, and a loading unit extending distally from the elongate body. The loading unit includes an anvil assembly and a staple cartridge assembly, and the staple cartridge assembly includes a surgical buttress attachment assembly. The surgical buttress attachment assembly includes a staple cartridge and a surgical buttress. The staple cartridge includes a cartridge body and a cartridge tip extending distally from the cartridge body. The cartridge body has a tissue facing surface including staple pockets defined therein and the cartridge tip includes an inner surface extending distally from the tissue facing surface and defining an opening therethrough that is in communication with a cavity defined in the cartridge tip. The cartridge tip includes a distal buttress attachment assembly having a block body disposed within the cavity and a distal tongue extending distally from the block body. The block body is movable between an extended position in which a distal end of the distal tongue is disposed over the inner surface of the cartridge tip and a retracted position in which the distal end of the distal tongue is aligned with the inner surface. The surgical buttress includes a proximal end portion releasably secured to the cartridge body and a distal end portion releasably secured to the cartridge tip by engagement of the distal tongue with the distal end portion when the block body is in the extended position.

The distal buttress attachment assembly may further include a resilient biasing member biasing the block body in the extended position. In some aspects, the resilient biasing member is a spring. In certain aspects, the spring includes a proximal end portion coupled to a distal-facing wall of the cartridge tip that defines the cavity and a distal end portion coupled to the block body, and the spring is compressible during axial movement of the block body between the extended and retracted positions. In some aspects, the resilient biasing member is a proximal arm extending from the block body. In certain aspects, the proximal arm abuts a distal-facing wall of the cartridge tip that defines the cavity, and the proximal arm is temporarily deformable against the distal-facing wall during rotational movement of the block body between the extended and retracted positions.

The staple cartridge may further include a proximal buttress attachment assembly including proximal posts extending outwardly from the tissue facing surface. The proximal end portion of the surgical buttress may be releasably secured to the cartridge body by engagement of the proximal posts with the proximal end portion. In some aspects, the proximal posts are proximal to the staple pockets. The proximal end portion of the surgical buttress may define proximal openings therethrough configured to receive the proximal posts therethrough, and the distal end portion of the surgical buttress may define a distal opening therethrough configured to receive the distal tongue therethrough.

The details of one or more aspects of this disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of this disclosure are described hereinbelow with reference to the drawings, which are incorporated in and constitute a part of this specification, wherein.

DETAILED DESCRIPTION

Figure 1:
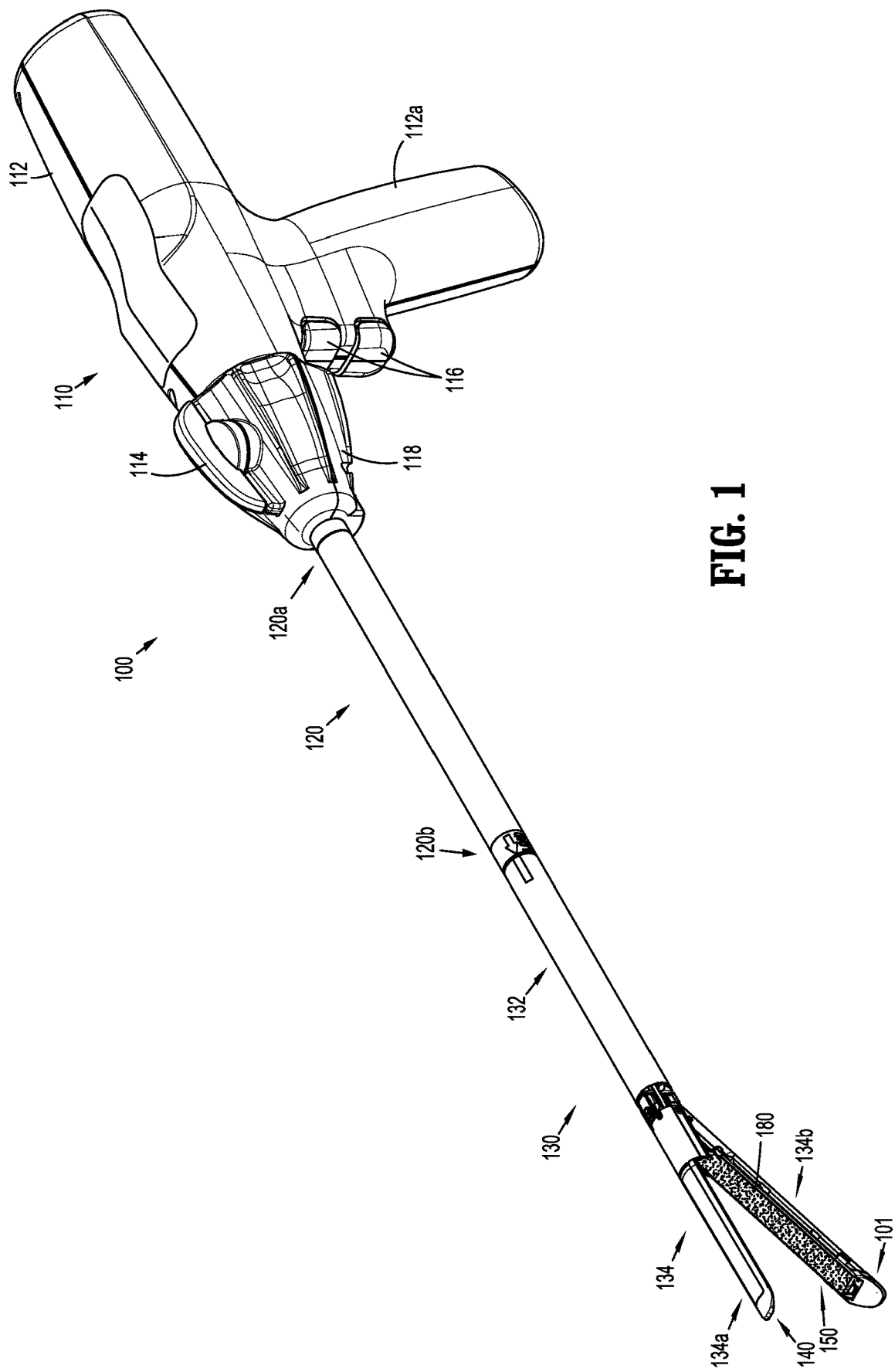
FIG. 1 is a perspective view of a surgical stapling apparatus in accordance with aspects of the disclosure.

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Further, it should be understood that various elements of the disclosure, such as those numbered in the 100 series, correspond to elements of the disclosure similarly numbered in the 200 series, such that redundant explanation of similar elements need not be repeated herein.

Turning now to FIG. 1, a surgical device or surgical stapling apparatus 100 is shown in accordance with aspects of the disclosure. The surgical stapling apparatus 100 generally includes a handle assembly 110, an elongate body or adapter assembly 120, and a loading unit 130. The handle assembly 110 is configured for selective connection with the elongate body 120 and, in turn, the elongate body 120 is configured for selective connection with the loading unit 130.

The surgical stapling apparatus 100 will further be described to the extent necessary to disclose aspects of the disclosure. For a detailed description of the structure and function of an exemplary surgical device suitable for use with a surgical buttress attachment assembly of the disclosure, reference may be made to U.S. patent application Ser. No. 17/329,711, the entire contents of which are incorporated herein by reference.

The handle assembly 110 includes a housing 112 that forms a stationary handle portion 112a, an articulation lever 114, and actuation buttons 116. The articulation lever 114 is operatively coupled to the loading unit 130 such that manipulation of the articulation lever 114 causes articulation of a tool assembly 134 of the loading unit 130 relative to the elongate body 120. The actuation buttons 116 control operation of the different functions of the surgical stapling apparatus 100 including, for example, clamping and firing of the surgical stapling apparatus 100.

The elongate body 120 includes a proximal portion 120a that is coupled to the handle assembly 110, and a distal portion 120b that supports the loading unit 130. The elongate body 120 is supported within a rotation knob 118 that is rotatably coupled to the handle assembly 110. The rotation knob 118 is manually rotatable to rotate the elongate body 120 and the loading unit 130 relative to handle assembly 110.

The loading unit 130 includes a proximal housing portion 132 that forms an extension of the elongate body 120 and a tool or jaw assembly 134 including first and second jaws 134a, 134b. The first jaw 134a and/or the second jaw 134b is pivotable with respect to the housing portion 132 such that the tool assembly 134 is movable between an open position in which the first and second jaws 134a, 134b are spaced apart with respect to each other, and a closed position in which the first and second jaws 134a, 134b are substantially adjacent each other.

Figure 2:
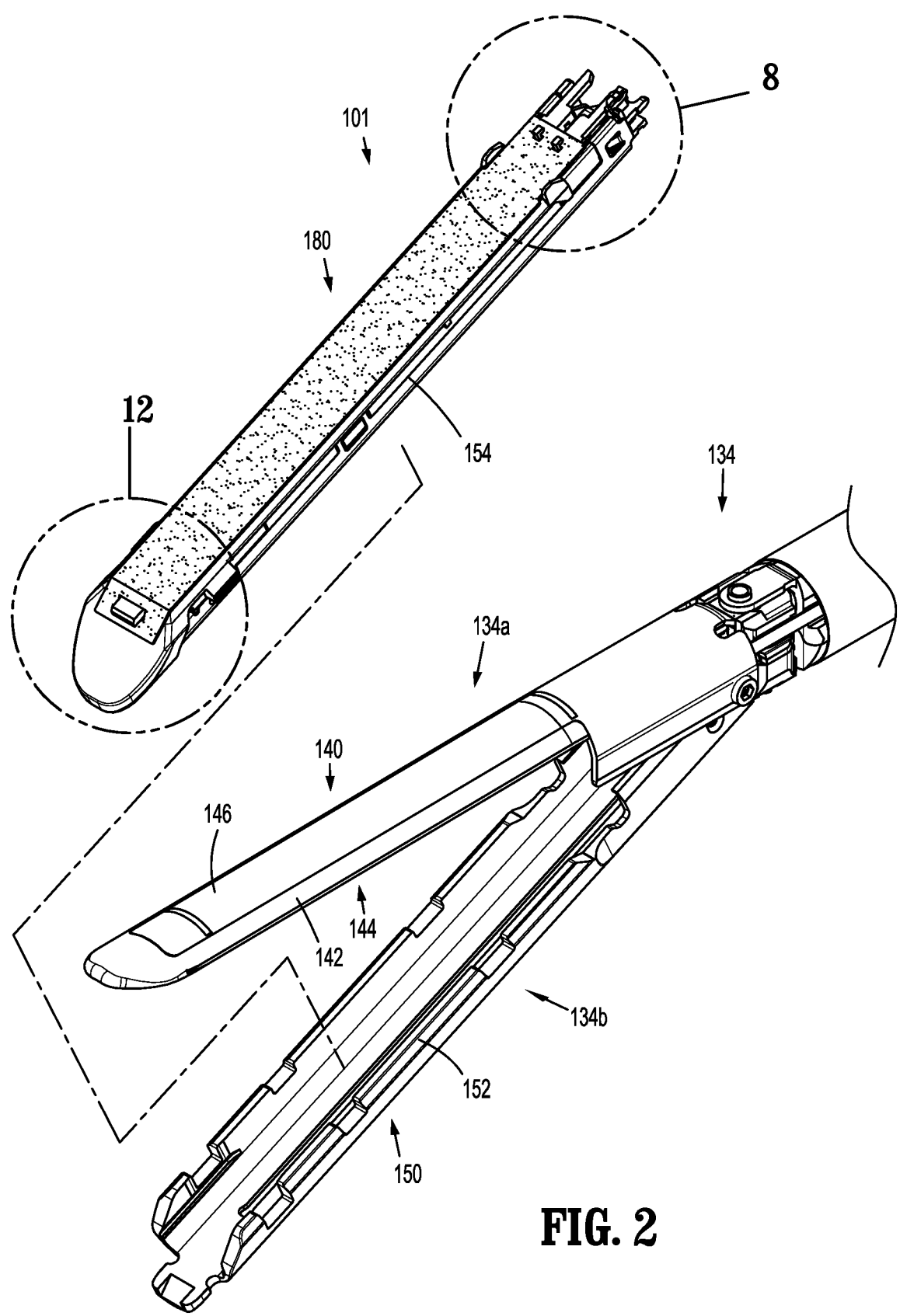
FIG. 2 is a perspective view of a tool assembly of the surgical stapling apparatus of FIG. 1, shown with a surgical buttress attachment assembly, which includes a staple cartridge and a surgical buttress, separated from first and second jaws of the tool assembly.

The loading unit 130 is a disposable loading unit ("DLU") that is releasably secured to the elongate body 120 and thus, replaceable with a new loading unit 130. The loading unit 130 may be a single use loading unit ("SULU") that is used one time and then replaced to facilitate multiples uses of the surgical stapling apparatus 100 on a patient. For example, during a surgical procedure, the surgical stapling apparatus 100 can be used to staple and cut tissue, and the entire SULU is replaced after each staple and cut operation of the surgical stapling apparatus 100. The loading unit 130 may be a multi-use loading unit ("MULU") that is re-useable a pre-determined number of times. For example, during a surgical procedure, the surgical stapling apparatus 100 can be used to staple and cut tissue, and a reload (e.g., a staple cartridge 154, as seen in FIG. 2) of the MULU is replaced after each staple and cut operation of the surgical stapling apparatus 100 a pre-determined number of times before the entire MULU needs to be replaced. Alternatively, the loading unit 130 may be permanently affixed (e.g., fixedly coupled) to the elongate body 120.

FIGS. 1 and 2 illustrate the first jaw 134a of the tool assembly 134, which includes an anvil assembly 140, and the second jaw 134b of the tool assembly 134, which includes a staple cartridge assembly 150 having a surgical buttress 180 releasably attached thereto. The anvil assembly 140 includes an anvil plate 142 having a tissue facing surface 144, and a cover plate 146 secured over the anvil plate 142. The staple cartridge assembly 150 includes a cartridge carrier 152 and a staple cartridge 154 selectively received and supported within the cartridge carrier 152. The staple cartridge 154 may be removably and/or replaceably attached to the cartridge carrier 152 by, for example, a snap-fit connection, a detent, a latch, among other types of connectors within the purview of those skilled in the art. Together the staple cartridge 154 and the surgical buttress 180 form a surgical buttress attachment assembly 101.

Figure 3:
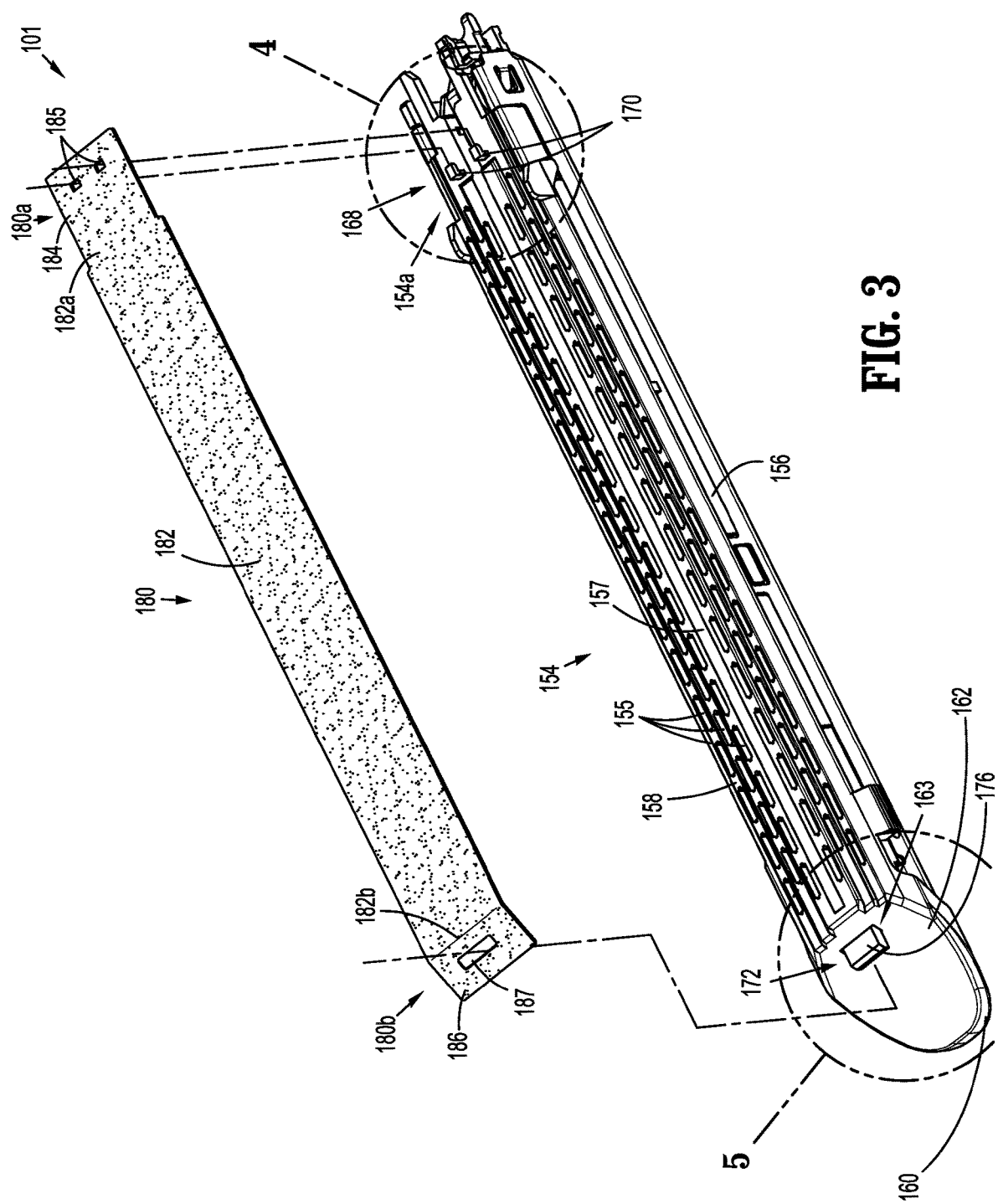
FIG. 3 is a perspective view of the surgical buttress attachment assembly of FIG. 2, shown with the surgical buttress separated from the staple cartridge.

With reference now to FIG. 3, the staple cartridge 154 includes a cartridge body 156 having an inner or tissue facing surface 158 defining staple pockets or retention slots 155 that support staples (not shown) therein. A central longitudinal slot 157 is also defined in the tissue facing surface 158 and extends along a substantial length of the cartridge body 156 to facilitate passage of a knife (not shown) therethrough. A cartridge tip 160 extends from the cartridge body 156 distal to the staple pockets 155. The cartridge tip 160 includes an inner surface 162 contiguous with and extending distally from the tissue facing surface 158 of the cartridge body 156. The inner surface 162 has an opening 163 defined therein that is in communication with a cavity 161 (FIG. 6) defined in the cartridge tip 160. The inner surface 162 may be angled or taper distally from the cartridge body 156.

A proximal buttress attachment assembly 168 is associated with the cartridge body 156 and a distal buttress attachment assembly 172 is associated with the cartridge tip 160. The proximal buttress attachment assembly 168 is a fixed assembly in which components thereof are rigid and do not move relative to the staple cartridge 154, and the distal buttress attachment assembly 172 is a variable assembly in which one or more components thereof are movable relative to the staple cartridge 154.

Figure 4:
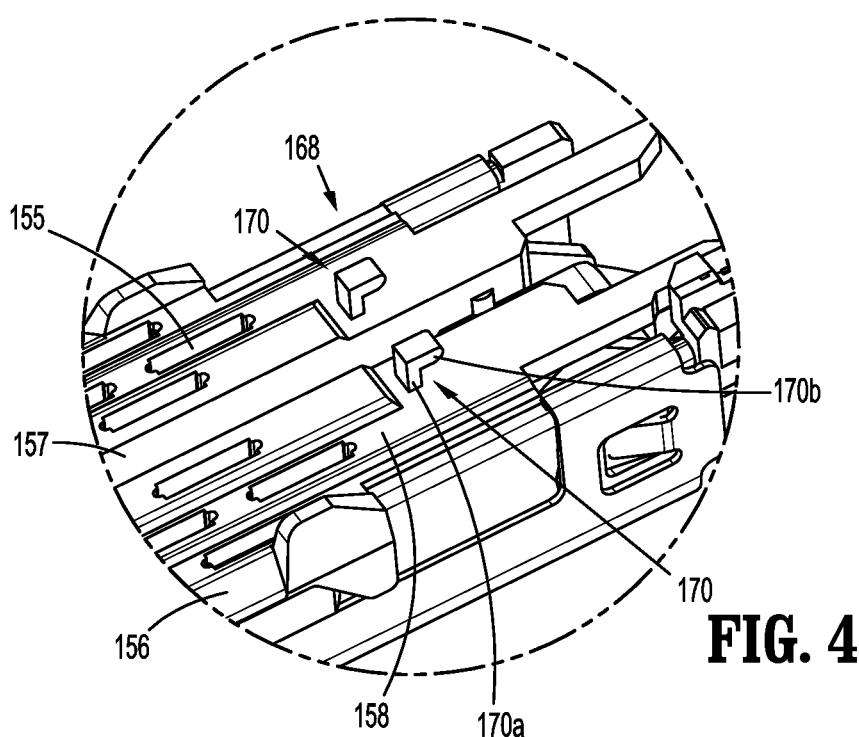
FIG. 4 is a close-up view of the area of detail 4 indicated in FIG. 3, showing a proximal end portion of the staple cartridge of the surgical buttress attachment assembly.

As shown in FIGS. 3 and 4, the proximal buttress attachment assembly 168 includes proximal posts 170 disposed on the tissue facing surface 158 of the cartridge body 156 proximal to the staple pockets 155. The proximal posts 170 are disposed on opposed sides of the central longitudinal slot 157 of the cartridge body 156. Each of the proximal posts 170 is axially aligned with an innermost row of staple pockets 155, however, it should be understood that the proximal posts 170 may be otherwise laterally positioned relative to the staple pockets 155. Each of the proximal posts 170 includes an elongate body 170a extending outwardly from the tissue facing surface 158 of the cartridge body 156 towards the anvil assembly 140 (FIG. 2). The elongate bodies 170a may be pins, poles, columns, etc. among other types of projections within the purview of those skilled in the art to which a proximal end portion 180a of the surgical buttress 180 may be secured. Each of the proximal posts 170 further includes a flange or hook 170b extending proximally from the elongate body 170a to aid in retaining the proximal end portion 180a of the surgical buttress 180 on the staple cartridge 154.

While the elongate bodies 170a of the proximal posts 170 are shown as extending along an axis that is substantially orthogonal to an axis defined by the tissue facing surface 158 of the cartridge body 156 and the hooks 170b are shown as extending along an axis substantially parallel to an axis defined by the tissue facing surface 158 of the cartridge body 156, it should be understood that the proximal posts 170, or components thereof, may extend at other orientations relative to the tissue facing surface 158, such as at a proximally extending angle. The proximal posts 170 may be secured to or integrally formed with the tissue facing surface 158 of the cartridge body 156. In some aspects, the proximal posts 170 are components added to the staple cartridge 154 and, in some other aspects, the staple cartridge 154 is molded to include the proximal posts 170.

Figure 5:
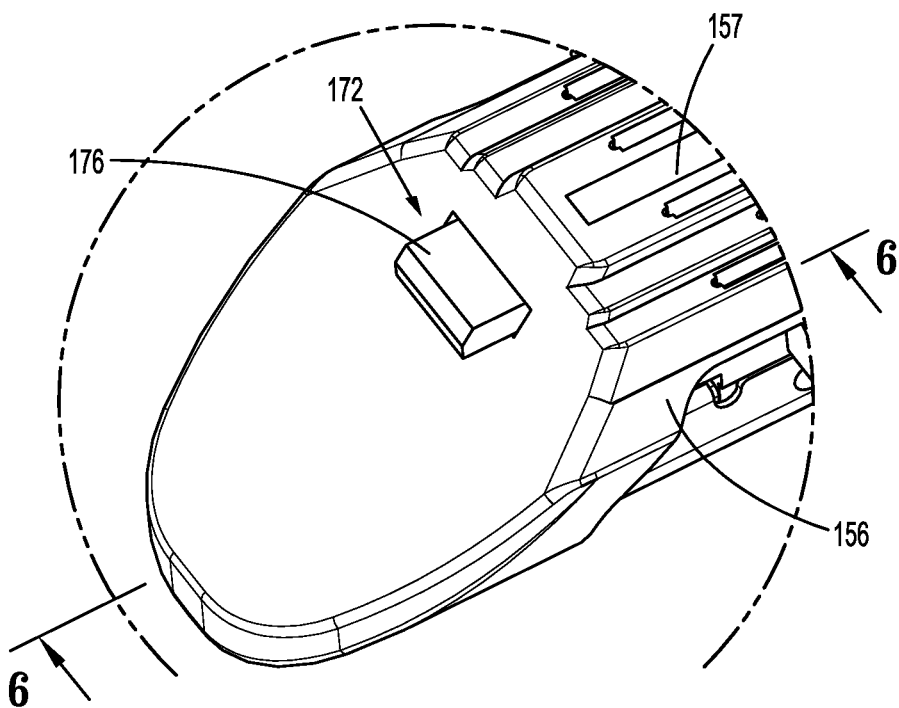
FIG. 5 is a close-up view of the area of detail 5 indicated in FIG. 3, showing a distal end portion of the staple cartridge of the surgical buttress attachment assembly.
Figure 6:
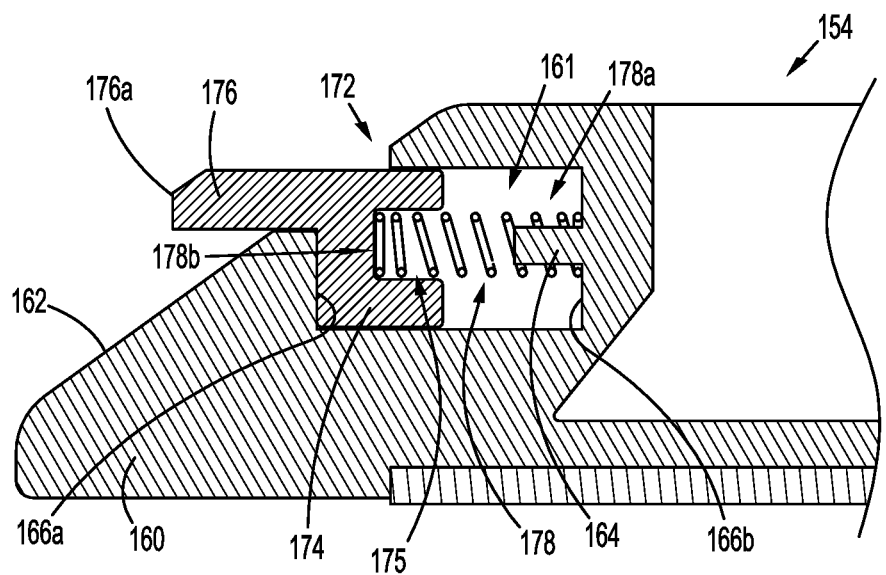
FIG. 6 is a cross-sectional view of the staple cartridge of FIG. 5, taken along section line 6-6 of FIG. 5, showing a distal buttress attachment assembly of the surgical buttress attachment assembly.
Figure 7:
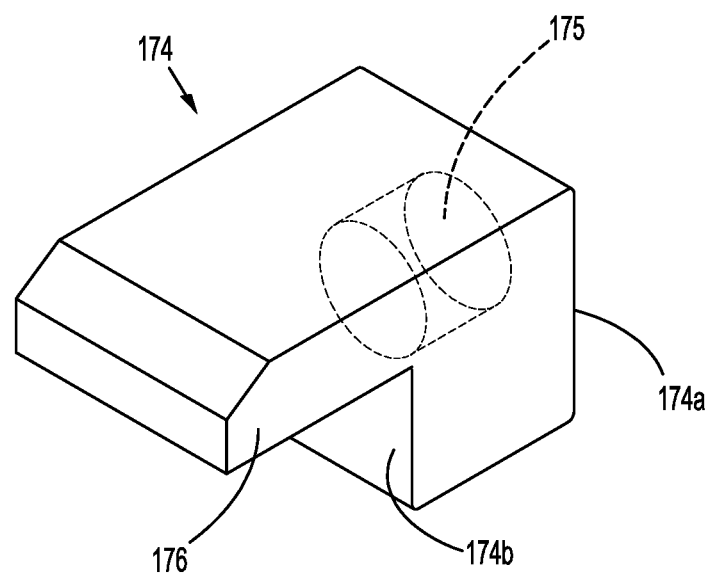
FIG. 7 is a perspective view of a block body of the distal buttress attachment assembly of FIG. 6.

As shown in FIGS. 5-7, the distal buttress attachment assembly 172 includes a block body 174 and a spring 178 disposed within a cavity 161 defined in the cartridge tip 160. The block body 174 includes a retention slot 175 defined therein that is open at a proximal end 174a of the block body 174 and a distal tongue 176 extending distally from a distal end 174b of the block body 174. A proximal end portion 178a of the spring 178 is disposed around a post 164 that is disposed within the cavity 161 and extends distally from a distal-facing wall 166b of the staple cartridge 154 that defines the cavity 161. A distal end portion 178b of the spring 178 is disposed within the retention slot 175 of the block body 174. The spring 178 biases the block body 174 distally such that the distal end 174b of the block body 174 abuts a proximal-facing wall 166a of the staple cartridge 154 that defines the cavity 161, and the distal tongue 176 extends out of the cavity 161 and over the inner surface 162 of the cartridge tip 160, as seen in FIG. 6. It should be understood that while the distal buttress attachment assembly 172 is shown including a coil spring, other resilient biasing members within the purview of those skilled in the art, such as a diaphragm spring, may be utilized in the distal buttress attachment assembly 172.

Figure 10:
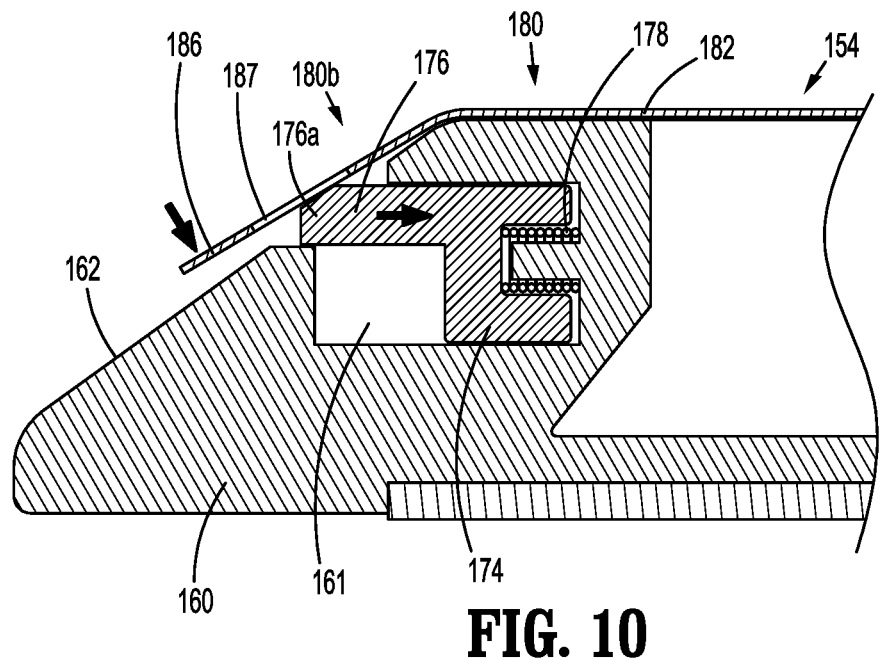
FIG. 10 is a cross-sectional view of the surgical buttress attachment assembly of FIG. 9, taken along section line 10-10 of FIG. 9, showing the distal buttress attachment assembly in a retracted position.

The cavity 161 of the cartridge tip 160 is sized and shaped to retain the block body 174 of the distal buttress attachment assembly 172 therein such that the block body 174 is axially movable between an extended or distal position (FIG. 6) and a retracted or proximal position (FIG. 10). When in the extended position, a distal end 176a of the distal tongue 176 extends outwardly over the inner surface 162 of the cartridge tip 160, and when in the retracted position, the distal end 176a of the distal tongue 176 is substantially aligned with the inner surface 162 or may be disposed within the cavity 161 of the cartridge tip 160 so that the distal end 176a does not extend over the inner surface 162 of the cartridge tip 160.

The distal tongue 176 is axially aligned with the central longitudinal slot 157 (FIG. 5) defined in the cartridge body 156 for retaining a distal end portion 180b (FIG. 3) of the surgical buttress 180 on the staple cartridge 154. While the distal tongue 176 is shown as extending along an axis that is substantially parallel to an axis defined by the tissue facing surface 158 of the cartridge body 156, similar to the proximal posts 170, the distal tongue 176 may have other configurations and/or orientations relative to the inner surface 162 of the cartridge tip 160 so long as the distal tongue 176 is configured to engage and retain the distal end portion 180b of the surgical buttress 180 on the staple cartridge 154 when in the extended position.

With reference again to FIG. 3, the surgical buttress 180 includes a body 182 having a generally rectangular shape that is configured for positioning over the staple pockets 155 of the tissue facing surface 158 of the staple cartridge 154. Proximal and distal end portions 180a, 180b of the surgical buttress 180 respectively include proximal and distal tabs 184, 186. The proximal and distal tabs 184, 186 respectively extend proximally and distally from proximal and distal ends 182a, 182b of the body 182. The proximal and distal tabs 184, 186 may be delineated from the body 182 by perforations (not shown) extending transversely through the surgical buttress 180.

The proximal tab 184 is sized and shaped for positioning over a proximal end portion 154a of the staple cartridge 154 that is proximal to the staple pockets 155 and the distal tab 186 is sized and shaped for positioning over the cartridge tip 160. While the proximal tab 184 is shown as having a width that is less than the width of the body 182 and the distal tab 186 is shown as having a width that is substantially the same as the width of the body 172, it should be understood that the proximal and distal tabs 184, 186 may have other sizes and shapes so long as they are configured to engage the proximal posts 170 and the distal tongue 176, respectively, of the staple cartridge 154, as described below.

The proximal tab 184 includes proximal openings 185 defined therethrough that are sized and shaped to engage the proximal posts 170 of the cartridge body 156. The distal tab 186 includes a distal opening 187 defined therethrough that is sized and shaped to engage the distal tongue 176 of the cartridge tip 160. The proximal and distal openings 185, 187 are pre-formed and may be in the form of holes, slots, slits, etc. so long as the proximal and distal tabs 184, 186 can frictionally engage the respective proximal posts 170 and distal tongue 176 via the proximal and distal openings 185, 187. Further, the proximal and distal openings 185, 187 are positioned in the respective proximal and distal tabs 184, 186 such that when the surgical buttress 180 is loaded onto the staple cartridge 154 the surgical buttress 180 is flush with the staple cartridge 154.

The surgical buttress 180 is fabricated from biocompatible materials which are bioabsorbable or non-absorbable, natural or synthetic materials. It should be understood that a single or combination of natural, synthetic, bioabsorbable, and/or non-bioabsorbable materials may be used to form the surgical buttress 180. In aspects, the surgical buttress 180 is a single sheet of material that is formed and cut to shape. In other aspects, the surgical buttress 180 is formed from a plurality of sheets of material, that are fabricated from the same or different materials, and/or the components (e.g., the body, the proximal tab, the distal tab, etc.) of the surgical buttress 180 are formed from the same or different materials that are attached to one another by, for example, welding, using adhesive, tying sutures, etc.

The surgical buttress 180 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttress 180 may be a single porous or non-porous layer, or include a plurality of layers including any combination of porous and non-porous layers. For example, the surgical buttress 180 may include multiple porous and non-porous layers that are stacked in an alternating manner. In another example, the surgical buttress 180 may be formed in a "sandwich-like" manner wherein the outer layers are porous and the inner layer(s) are non-porous, or vice versa.

Porous layer(s) in the surgical buttress 180 may enhance the ability of the surgical buttress 180 to absorb fluid, reduce bleeding, and/or seal a wound. Also, the porous layer(s) may allow for tissue ingrowth to fix the surgical buttress 180 in place. Non-porous layer(s) in the surgical buttress 180 may enhance the ability of the surgical buttress 180 to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

Figure 8:
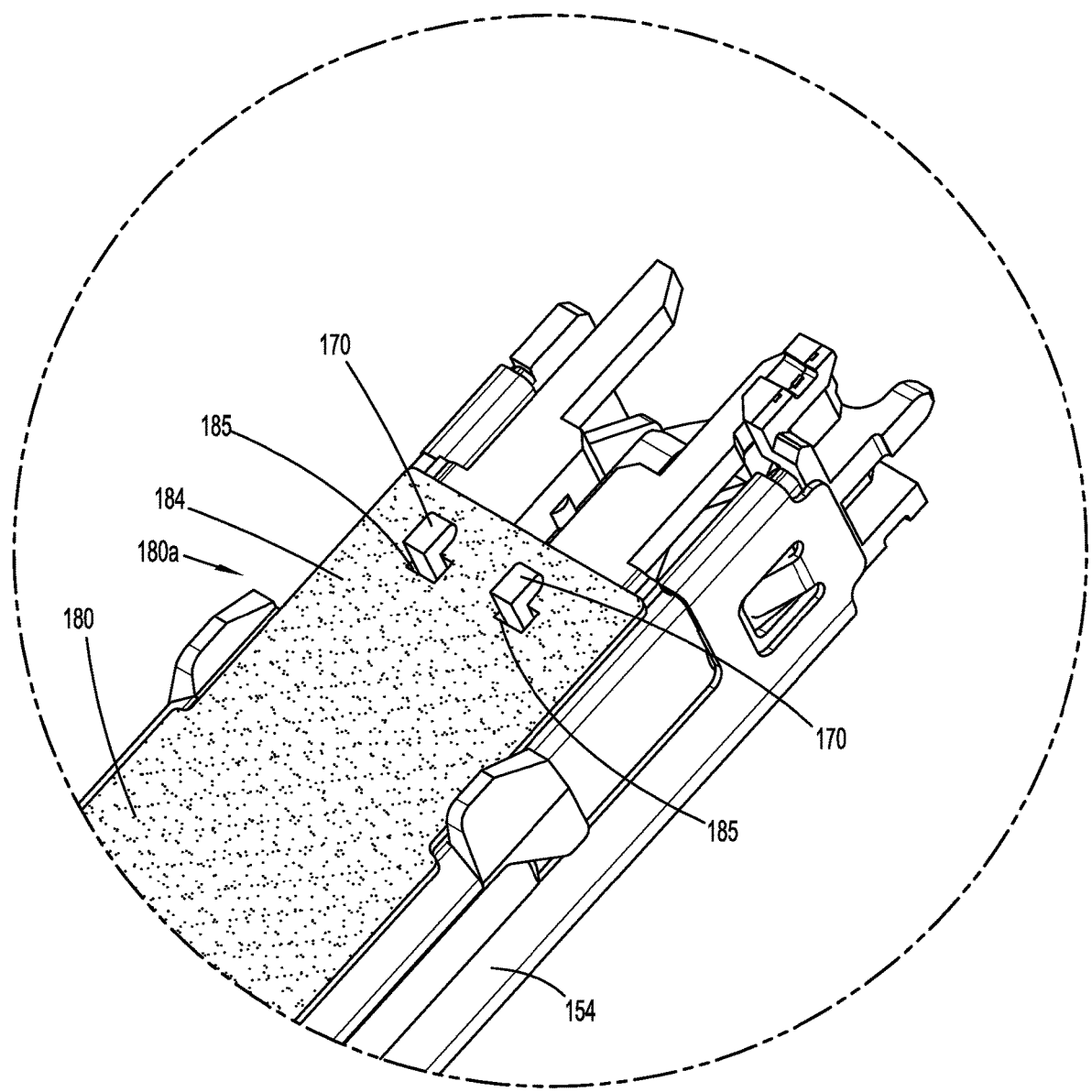
FIG. 8 is a close-up view of the area of detail 8 indicated in FIG. 2, showing a proximal end portion of the surgical buttress secured to a proximal end portion of the staple cartridge via a proximal buttress attachment assembly of the surgical buttress attachment assembly.
Figure 9:
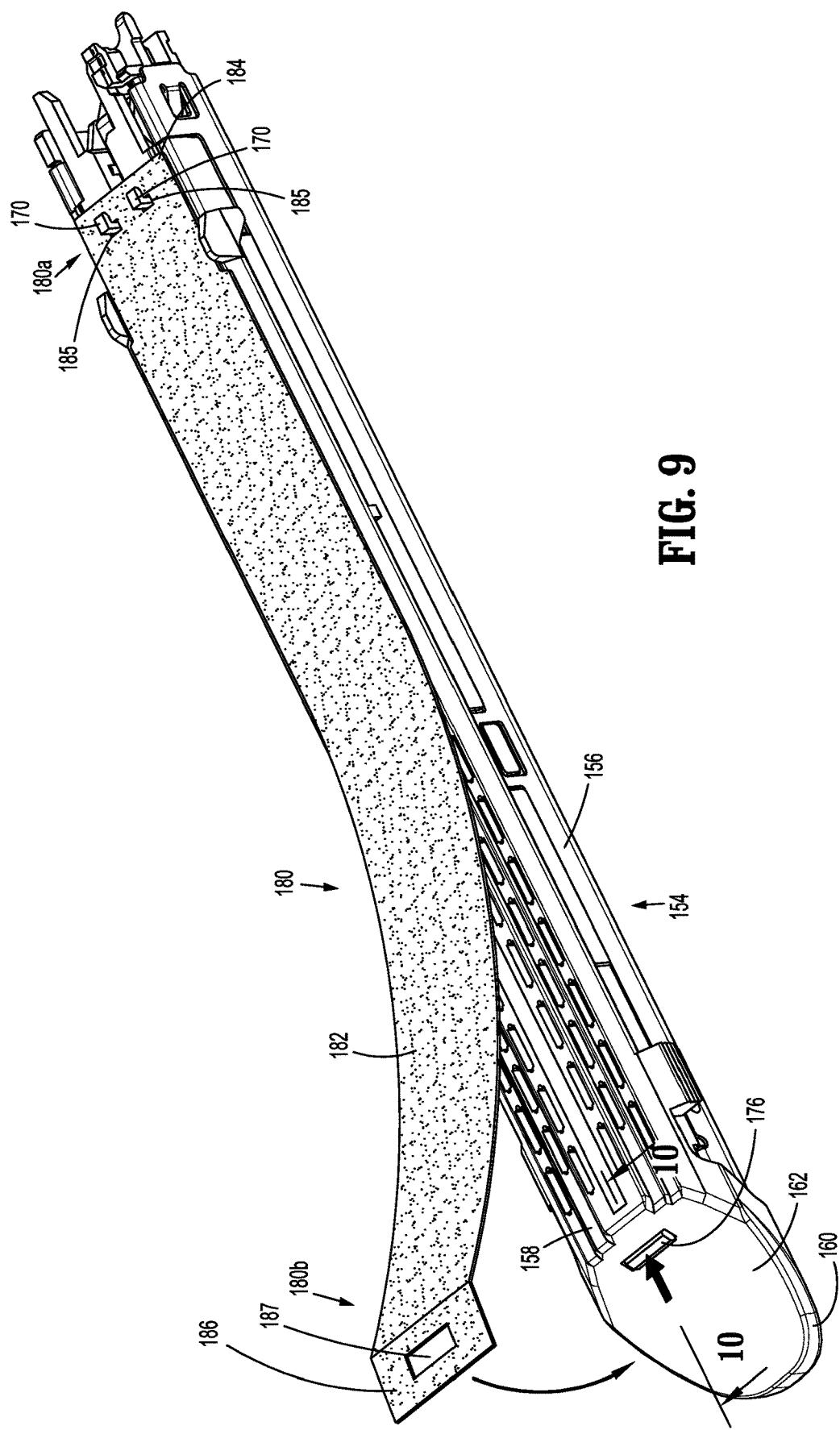
FIG. 9 is a perspective view of the surgical buttress attachment assembly of FIG. 3, showing the surgical buttress partially loaded on the staple cartridge.

In a method of loading the surgical buttress 180 onto the staple cartridge 154, as initially seen in FIG. 3, the surgical buttress 180 is positioned over the tissue facing surface 158 of the staple cartridge 154 such that the proximal and distal tabs 184, 186 are respectively aligned with the proximal and distal buttress retention assemblies 168, 172 of the staple cartridge 154. The proximal end portion 180a of the surgical buttress 180 is moved towards the staple cartridge 154 so that the proximal posts 170 of the staple cartridge 154 extend through the proximal openings 185 of the surgical buttress 180 and engage the proximal tab 184 to retain the proximal end portion 180a of the surgical buttress 180 on the staple cartridge 154, as seen in FIGS. 8 and 9. The body 182 is laid upon the tissue facing surface 158 of the staple cartridge 156 and the distal tongue 176 of the distal buttress attachment assembly 172 is pressed distally into the cavity 161 of the cartridge tip 160 to move the block body 174 to the retracted position, as seen in FIGS. 9 and 10. The distal end portion 180b of the surgical buttress 180 is laid upon the inner surface 162 of the cartridge tip 160 so that the body 182 of the surgical buttress 180 lies flush against the tissue facing and inner surfaces 158, 162 of the staple cartridge 154

Figure 11:
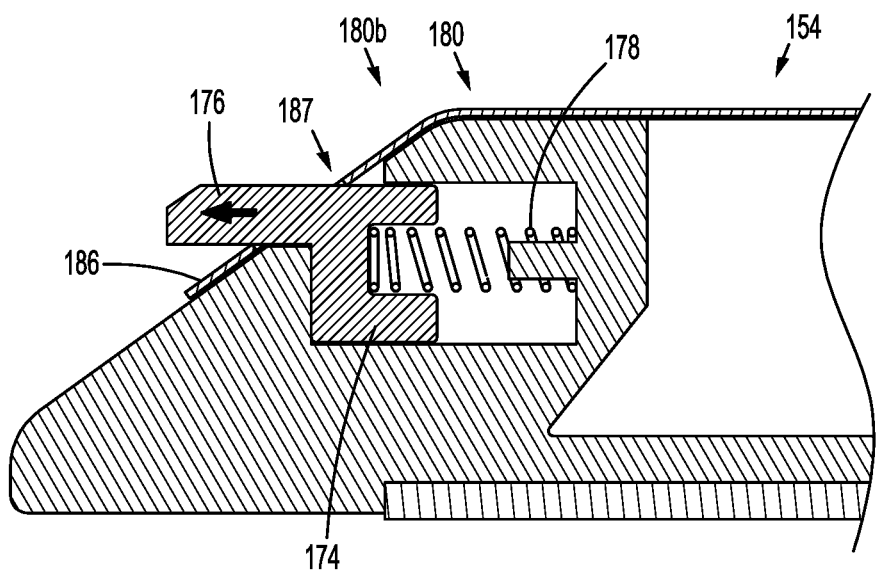
FIG. 11 is a cross-sectional view of the surgical buttress attachment assembly of FIG. 10, showing the distal buttress attachment assembly in an extended position.
Figure 12:
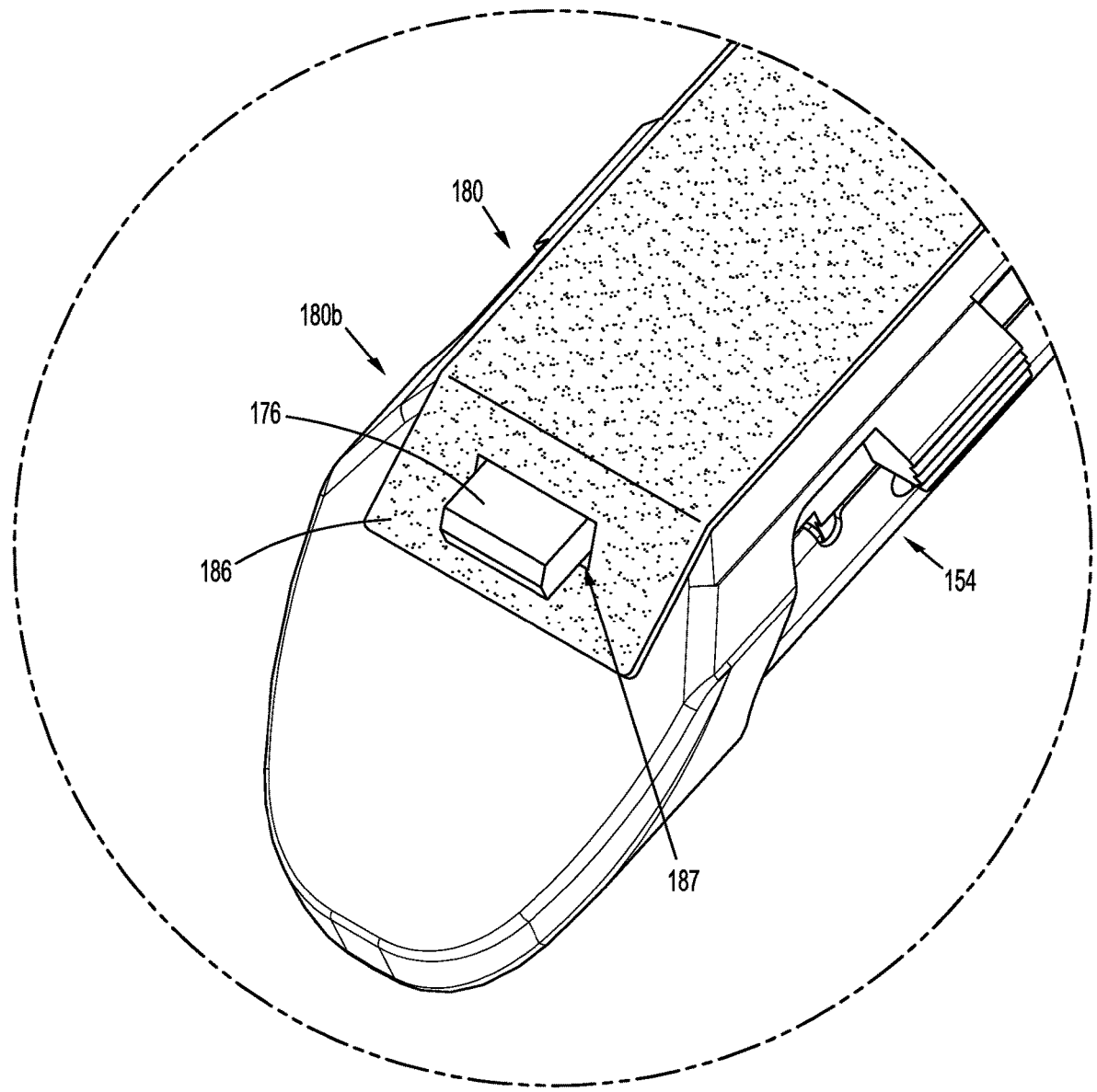
FIG. 12 is a close-up view of the area of detail 12 indicated in FIG. 2, showing a distal end portion of the surgical buttress secured to a distal end portion of the staple cartridge via the distal buttress attachment assembly.

(without deforming the surgical buttress 180 during the loading process) and the distal opening 187 of the surgical buttress 180 is aligned with the distal tongue 176. The distal tongue 176 is released and the block body 174 returns to its biased, extended position, as shown in FIGS. 11 and 12. Upon movement from the retracted to the extended position, the distal tongue 176 moves through the distal opening 187 and engages the distal tab 186 of the surgical buttress 180 to retain the distal end portion 180b of the surgical buttress 180 on the staple cartridge 154. The staple cartridge 154 is now loaded with the surgical buttress 180. The staple cartridge 154 may be pre-loaded with the surgical buttress 180 (e.g., by the manufacturer) or may be loaded with the surgical buttress 180 (e.g., by an end-user).

The surgical stapling apparatus 1 (FIG. 1), with the staple cartridge assembly 150 including the assembled surgical buttress attachment assembly 101, is ready for use. The surgical stapling apparatus 1 is used in accordance with methods known by those skilled in the art. Once the anvil and staple cartridge assemblies 140, 150 are clamped onto tissue, the surgical stapling apparatus 1 is fired, thereby stapling the surgical buttress 180 to the tissue. During firing, a knife (not shown) travels distally between the anvil and staple cartridge assembly 140, 150 and substantially simultaneously cuts and divides the tissue and the surgical buttress 180 disposed between the rows of formed staples. When firing is complete and the anvil and staple cartridge assemblies 140, 150 are unclamped, the surgical buttress 180, which is now stapled to the tissue, pulls away from the staple cartridge assembly 150, and the tool assembly 134 can be removed from the surgical site. The used staple cartridge 154 may then be removed from the tool assembly 134 and replaced with a new staple cartridge 154. A new surgical buttress 180 may be installed onto the new staple cartridge 154, as needed or desired, as described above.

Figure 13:
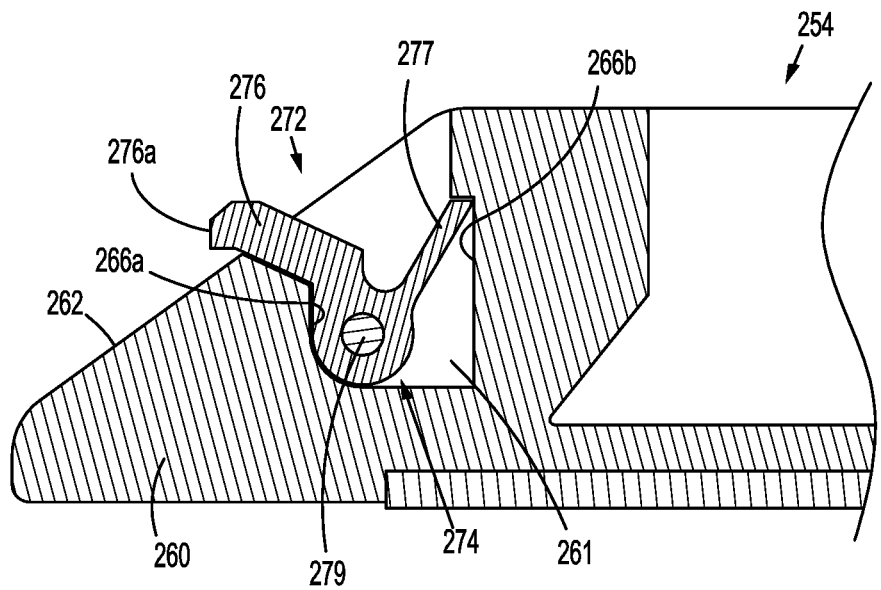
FIG. 13 is a partial, cross-sectional view of a staple cartridge including a distal buttress attachment assembly in accordance with another aspect of the disclosure.
Figure 14:
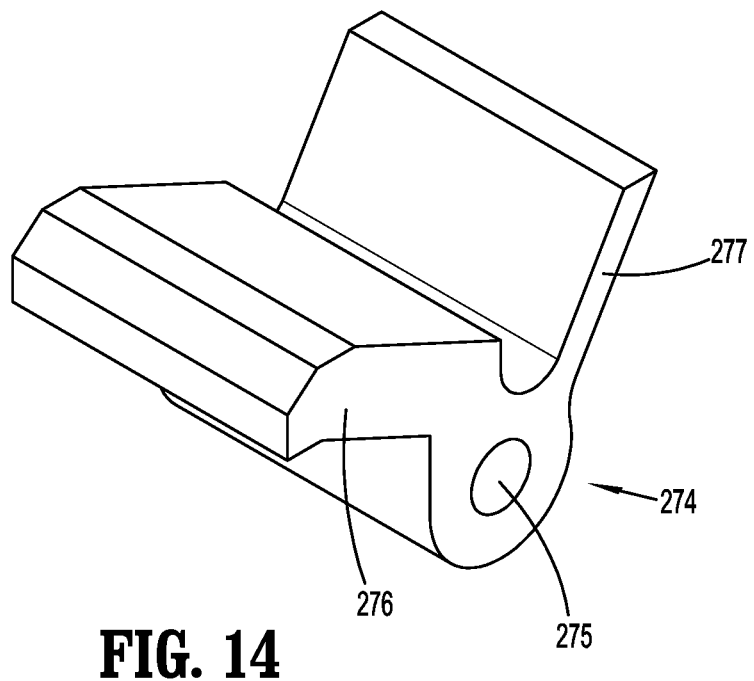
FIG. 14 is a perspective view of a block body of the distal buttress attachment assembly of the staple cartridge of FIG. 13.

Turning now to FIG. 13, a staple cartridge 254 in accordance with another aspect of the disclosure is shown. The staple cartridge 254 is substantially the same as the staple cartridge 154, except that the cartridge tip 260 defines a cavity 261 housing a distal buttress attachment assembly 272 including a block body 274 and a pivot pin 279. As shown in FIGS. 13 and 14, the block body 274 includes a retention slot 275 defined therethrough, a distal tongue 276 extending distally from the block body 274, and a proximal arm 277 extending proximally from the block body 274. The pivot pin 279 extends through the retention slot 275 and is engaged with the cartridge tip 260 such that the block body 274 is pivotable about the pivot pin 276. The proximal arm 277 biases the block body 274 towards an extended position by engagement of the proximal arm 277 with a distal-facing wall 266b of the cavity 261 such that the distal tongue 276 abuts an angled segment of a proximal-facing wall 266a and extends out of the cavity 261 and over the inner surface 262 of the cartridge tip 260. The proximal arm 277 is flexible and temporarily deformable upon application of a force thereto, as described below.

Figure 15:
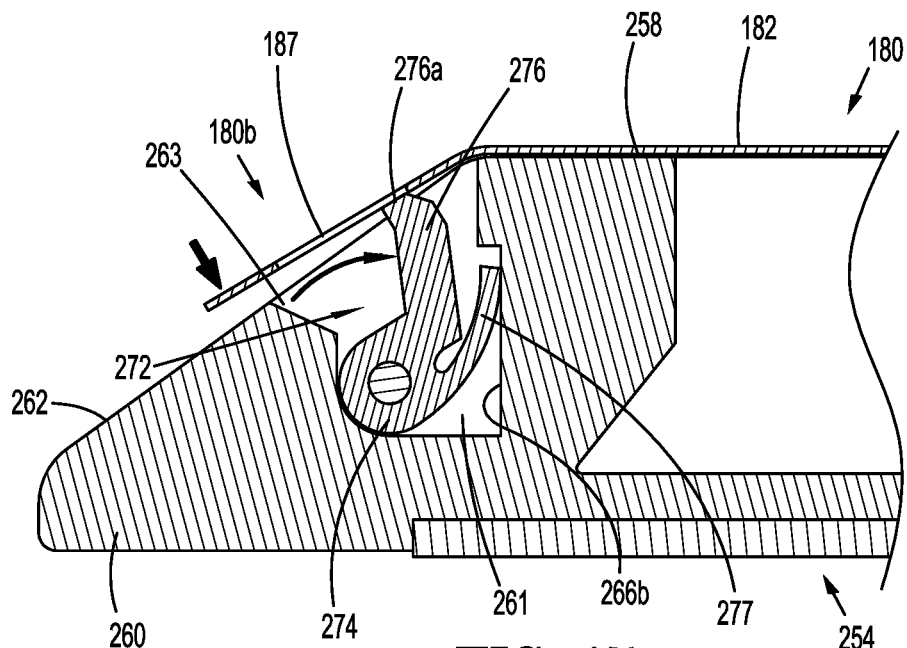
FIG. 15 is a partial, cross-sectional view of a surgical buttress attachment assembly including the staple cartridge of FIG. 13 and a surgical buttress, shown with the distal buttress attachment assembly in a retracted position.

The cavity 261 of the cartridge tip 260 is sized and shaped to retain the block body 274 of the distal buttress attachment assembly 272 therein such that the block body 274 is axially movable between an extended or distal position (FIG. 13) and a retracted or proximal position (FIG. 15). When in the extended position, the distal tongue 276 extends outwardly over the inner surface 262 of the cartridge tip 260, and when in the retracted position, a distal end 276a of the distal tongue 276 is substantially aligned with the inner surface 262 or may be disposed within the cavity 261 of the cartridge tip 260.

Figure 16:
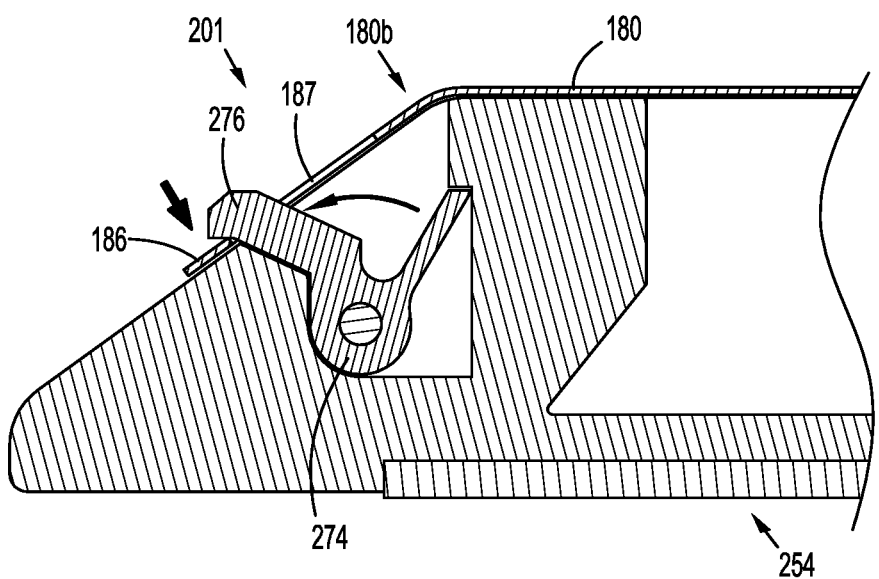
FIG. 16 is a partial, cross-sectional view of the surgical buttress attachment assembly of FIG. 15, shown with the distal buttress attachment assembly in an extended position.

In a method of loading a surgical buttress 180 (FIG. 15) onto the staple cartridge 254, the surgical buttress 180 is positioned over the tissue facing surface 258 of the staple cartridge 254 and the proximal tab (not shown) of the surgical buttress 180 is engaged with the proximal buttress retention assembly (not shown) of the staple cartridge 254 as described above with regard to FIG. 8. The body 182 of the surgical buttress 180 is laid upon the tissue facing surface 258 of the staple cartridge 254 and the block body 274 is pivoted to the retracted position, as shown in FIG. 15, by pushing the distal tongue 276 of the distal buttress attachment assembly 272 proximally so that the block body 274 rotates within the cavity 261 of the cartridge tip 260. During rotation, the proximal arm 277 is deformed against the distal-facing wall 266b. The distal end portion 180b of the surgical buttress 180 is then laid upon the inner surface 262 of the cartridge tip 260 so that the distal opening 187 is aligned with the opening 263 defined in the inner surface 262. The distal tongue 276 is released and the block body 274 returns to its biased extended position, as shown in FIG. 16, so that the distal tongue 276 extends through the distal opening 187 and engages the distal tab 186 of the surgical buttress 180 to capture and retain the distal end portion 180b of the surgical buttress 180 on the staple cartridge 254. The staple cartridge 254 is now loaded with the surgical buttress 180. The surgical stapling apparatus 1 (FIG. 1), with the assembled surgical buttress attachment assembly 201 (FIG. 16), is used as described above with regard to the surgical buttress attachment assembly 101 of FIG. 2.

It should be understood that the anvil assembly 140 (FIG. 1) may be pre-loaded and/or loaded with a surgical buttress. The surgical buttress may be retained on the anvil assembly by any suitable attachment feature within the purview of those skilled in the art, such as, for example, mechanical attachment features (e.g., a suture), chemical attachment features (e.g., adhesive), and/or attachment methods (e.g., welding). Further, while the surgical buttress attachment assemblies of this disclosure are described and shown for surgical buttress attachment on the second jaw of the tool assembly, it should be understood that surgical buttress attachment assemblies may additionally or alternatively be configured for use on the first jaw of the tool assembly. For example, the anvil assembly may include a proximal or distal buttress attachment assembly similar to those shown on the staple cartridge.

While illustrated as being used on a handheld powered surgical device hereinabove, it is contemplated, and within the scope of the disclosure for the surgical buttress attachment assemblies to be configured for use with other handheld powered or manually-actuated surgical devices, as well as other electrosurgical instruments. For example, the surgical buttress attachment assemblies may be used on handheld powered surgical devices, such as those shown and described in U.S. Pat. No. 10,426,468, and handheld manually actuated surgical devices, such as those shown and described in U.S. Pat. Nos. 4,473,077, 5,915,616, 5,964,394, 6,330,965, 7,128,253, and 7,334,717, the entire contents of each of which are incorporated herein by reference. As another example, the surgical buttress attachment assemblies may be used on robotic surgical systems, such as the robotic surgical system shown and described in U.S. Pat. No. 8,828,023, the entire contents of which are incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the disclosure, and that such modifications and variation are also included within the scope of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical buttress attachment assembly for use with a surgical stapling apparatus, the surgical buttress attachment assembly comprising:
   a staple cartridge including a cartridge body and a cartridge tip extending distally from the cartridge body, the cartridge body having a tissue facing surface including staple pockets defined therein and the cartridge tip including an inner surface extending distally from the tissue facing surface and defining an opening therethrough that is in communication with a cavity defined in the cartridge tip, the cartridge tip including a distal buttress attachment assembly having a block body disposed within the cavity and a distal tongue extending distally from the block body, the block body movable between an extended position in which a distal end of the distal tongue is disposed over the inner surface of the cartridge tip and a retracted position in which the distal end of the distal tongue is aligned with the inner surface; and
   a surgical buttress having a proximal end portion and a distal end portion, the proximal end portion releasably secured to the cartridge body and the distal end portion releasably secured to the cartridge tip by engagement of the distal tongue with the distal end portion when the block body is in the extended position.

2. The surgical buttress attachment assembly according to claim 1, wherein the tissue facing surface of the cartridge body includes a central longitudinal slot defined therein, and the distal tongue is axially aligned with the central longitudinal slot.

3. The surgical buttress attachment assembly according to claim 1, wherein the distal buttress attachment assembly further includes a resilient biasing member biasing the block body in the extended position.

4. The surgical buttress attachment assembly according to claim 3, wherein the resilient biasing member is a spring.

5. The surgical buttress attachment assembly according to claim 4, wherein the spring includes a proximal end portion coupled to a distal-facing wall of the cartridge tip that defines the cavity and a distal end portion coupled to the block body, the spring compressible during axial movement of the block body between the extended and retracted positions.

6. The surgical buttress attachment assembly according to claim 3, wherein the resilient biasing member is a proximal arm extending from the block body.

7. The surgical buttress attachment assembly according to claim 6, wherein the proximal arm abuts a distal-facing wall of the cartridge tip that defines the cavity, the proximal arm temporarily deformable against the distal-facing wall during rotational movement of the block body between the extended and retracted positions.

8. The surgical buttress attachment assembly according to claim 1, wherein the staple cartridge further includes a proximal buttress attachment assembly including proximal posts extending outwardly from the tissue facing surface, and the proximal end portion of the surgical buttress releasably secured to the cartridge body by engagement of the proximal posts with the proximal end portion.

9. The surgical buttress attachment assembly according to claim 8, wherein the proximal posts are proximal to the staple pockets.

10. The surgical buttress attachment assembly according to claim 8, wherein the tissue facing surface of the cartridge body includes a central longitudinal slot defined therein, and the proximal posts are disposed on opposed sides of the central longitudinal slot.

11. The surgical buttress attachment assembly according to claim 8, wherein the proximal end portion of the surgical buttress defines proximal openings therethrough configured to receive the proximal posts therethrough, and the distal end portion of the surgical buttress defines a distal opening therethrough configured to receive the distal tongue therethrough.

12. A surgical stapling apparatus, comprising:
   a handle assembly;
   an elongate body extending distally from the handle assembly; and
   a loading unit extending distally from the elongate body, the loading unit including an anvil assembly and a staple cartridge assembly, the staple cartridge assembly including a surgical buttress attachment assembly including:
      a staple cartridge including a cartridge body and a cartridge tip extending distally from the cartridge body, the cartridge body having a tissue facing surface including staple pockets defined therein and the cartridge tip including an inner surface extending distally from the tissue facing surface and defining an opening therethrough that is in communication with a cavity defined in the cartridge tip, the cartridge tip including a distal buttress attachment assembly having a block body disposed within the cavity and a distal tongue extending distally from the block body, the block body movable between an extended position in which a distal end of the distal tongue is disposed over the inner surface of the cartridge tip and a retracted position in which the distal end of the distal tongue is aligned with the inner surface; and
      a surgical buttress having a proximal end portion and a distal end portion, the proximal end portion releasably secured to the cartridge body and the distal end portion releasably secured to the cartridge tip by engagement of the distal tongue with the distal end portion when the block body is in the extended position.

13. The surgical stapling apparatus according to claim 12, wherein the distal buttress attachment assembly further includes a resilient biasing member biasing the block body in the extended position.

14. The surgical stapling apparatus according to claim 13, wherein the resilient biasing member is a spring.

15. The surgical stapling apparatus according to claim 14, wherein the spring includes a proximal end portion coupled to a distal-facing wall of the cartridge tip that defines the cavity and a distal end portion coupled to the block body, the spring compressible during axial movement of the block body between the extended and retracted positions.

16. The surgical stapling apparatus according to claim 13, wherein the resilient biasing member is a proximal arm extending from the block body.

17. The surgical stapling apparatus according to claim 16, wherein the proximal arm abuts a distal-facing wall of the cartridge tip that defines the cavity, the proximal arm temporarily deformable against the distal-facing wall during rotational movement of the block body between the extended and retracted positions.

18. The surgical stapling apparatus according to claim 12, wherein the staple cartridge further includes a proximal buttress attachment assembly including proximal posts extending outwardly from the tissue facing surface, and the proximal end portion of the surgical buttress releasably secured to the cartridge body by engagement of the proximal posts with the proximal end portion.

19. The surgical stapling apparatus according to claim 18, wherein the proximal posts are proximal to the staple pockets.

20. The surgical stapling apparatus according to claim 18, wherein the proximal end portion of the surgical buttress defines proximal openings therethrough configured to receive the proximal posts therethrough, and the distal end portion of the surgical buttress defines a distal opening therethrough configured to receive the distal tongue therethrough.

\* \* \* \* \*